United States Patent
Vigil et al.

[19]

[11] Patent Number: 5,873,852
[45] Date of Patent: *Feb. 23, 1999

[54] DEVICE FOR INJECTING FLUID INTO A WALL OF A BLOOD VESSEL

[75] Inventors: Dennis M Vigil, San Diego; Robert E. Reiss, La Jolla, both of Calif.; Peter Barath, Oak Brook, Ill.

[73] Assignee: Interventional Technologies, San Diego, Calif.

[*] Notice: The term of this patent shall not extend beyond the expiration date of Pat. No. 5,681,281.

[21] Appl. No.: 785,825

[22] Filed: Jan. 10, 1997

Related U.S. Application Data

[63] Continuation-in-part of Ser. No. 541,526, Oct. 10, 1995, Pat. No. 5,681,281, and a continuation-in-part of Ser. No. 500,121, Jul. 10, 1995, Pat. No. 5,716,716, and a continuation-in-part of Ser. No. 584,310, Jan. 11, 1996, Pat. No. 5,713,863.

[51] Int. Cl.$^6$ .................................................. A61M 31/00
[52] U.S. Cl. ............................. 604/52; 604/49; 604/96; 604/103; 604/191
[58] Field of Search .................. 604/19, 22, 48, 604/49, 50, 52, 53, 93, 96, 101, 103–109, 181, 183, 164, 191, 194, 198

[56] References Cited

U.S. PATENT DOCUMENTS

| | | |
|---|---|---|
| 2,816,552 | 12/1957 | Hoffman . |
| 3,593,713 | 7/1971 | Bogoff et al. . |
| 3,635,223 | 1/1972 | Klieman . |
| 4,140,126 | 2/1979 | Choudhury . |
| 4,273,128 | 6/1981 | Lary . |
| 4,318,400 | 3/1982 | Peery et al. . |
| 4,441,509 | 4/1984 | Kotsifas et al. . |
| 4,465,072 | 8/1984 | Taheri . |
| 5,009,659 | 4/1991 | Hamlin et al. . |
| 5,100,425 | 3/1992 | Fischell et al. . |
| 5,112,305 | 5/1992 | Barath et al. . |
| 5,156,610 | 10/1992 | Reger . |
| 5,196,024 | 3/1993 | Barath . |
| 5,242,397 | 9/1993 | Barath et al. . |
| 5,279,565 | 1/1994 | Klein et al. . |
| 5,282,785 | 2/1994 | Shapland et al. . |
| 5,286,254 | 2/1994 | Shapland et al. |
| 5,295,962 | 3/1994 | Crocker et al. . |
| 5,306,250 | 4/1994 | March et al. . . . |

(List continued on next page.)

FOREIGN PATENT DOCUMENTS

| | | |
|---|---|---|
| 0 399 712 A1 | 11/1990 | European Pat. Off. . |
| 0 567 788 A1 | 3/1993 | European Pat. Off. . |
| 1 547 328 | 6/1979 | United Kingdom . |
| WO 94/23787 | 10/1994 | WIPO . |

*Primary Examiner*—Wynn Wood Coggins
*Assistant Examiner*—Jennifer R. Sadola
*Attorney, Agent, or Firm*—Michael Klicpera

[57] ABSTRACT

A method and device for injecting fluid into a treatment area of a vessel wall is provided herein. A first version of the device includes an inflatable balloon mounted on a catheter and a plurality of injectors extending outwardly and moving with the balloon. At least one fluid passageway connects each injector in fluid communication with a fluid source. During use of the device, the balloon is first positioned in a vessel proximate the treatment area. Next, the balloon is inflated to embed the injectors into the vessel wall. Subsequently, the fluid from the fluid source is introduced into the fluid passageway and through the injectors into the treatment area. A second version of the device includes a plurality of flexible tubes mounted between a multi-lumen catheter and a grommet. A push-pull wire is connected to the grommet and passed through a lumen of the multi-lumen catheter. The injectors are mounted on each of the flexible tubes. During use, the device is first positioned in a vessel. The push-pull wire is then partially withdrawn forcing the grommet to advance towards the multi-lumen catheter. The advancing grommet forces the flexible tubes to bow outwardly, embedding the injectors into the vessel wall.

29 Claims, 5 Drawing Sheets

U.S. PATENT DOCUMENTS

| | | |
|---|---|---|
| 5,320,634 | 6/1994 | Vigil et al. . |
| 5,322,508 | 6/1994 | Viera . |
| 5,336,178 | 8/1994 | Kaplan et al. . |
| 5,354,279 | 10/1994 | Hofling . |
| 5,364,356 | 11/1994 | Hofling . |
| 5,370,614 | 12/1994 | Amundson et al. . |
| 5,415,637 | 5/1995 | Khosravi . |
| 5,571,086 | 11/1996 | Kaplan et al. . |
| 5,599,306 | 2/1997 | Klein et al. . |
| 5,609,574 | 3/1997 | Kaplan et al. . |
| 5,681,281 | 10/1997 | Vogel et al. ............................ 604/96 |

DEVICE FOR INJECTING FLUID INTO A WALL OF A BLOOD VESSEL

This is a continuation-in-part patent application of U.S. patent application Ser. No. 08/541,526, now U.S. Pat. No. 5,681,231 filed on Oct. 10, 1995 and entitled "Catheter With Fluid Medication Injectors" which is a continuation-in-part of patent application of U.S. patent application Ser. No. 08/500,121, now U.S. Pat. No. 5,716,716 filed on Jul. 10, 1995, and entitled "Catheter for Injecting Fluid Medication Into an Arterial Wall." This is also a continuation-in-part of patent application of U.S. patent application Ser. No. 08/584,310, now U.S. Pat. No. 5,713,863 filed on Jan. 11, 1996 and entitled "Catheter With Fluid Medication Injectors." The contents of the applications identified in this paragraph, are incorporated herein by reference.

FIELD OF THE INVENTION

The present invention pertains generally to medical devices useful for injecting fluid into a patient. More specifically, the present invention pertains to medical devices inserted into a vessel of a patient's cardiovascular system which are useful for injecting fluid directly into a vessel wall.

BACKGROUND

It is well known that fluid can be infused directly into wall of a blood vessel to treat some ailments. For example, medicaments can be administered into an arterial wall to inhibit or prevent the restenosis of plaque in the artery.

Due to the toxic nature of some fluids, the procedure must insure that only minimal amounts of medication are washed away into the blood stream and not actually infused into the vessel wall. Thus, the device for administering the fluid into the arterial wall must be easy to use, accurate and reliable.

Several devices have been suggested for the purpose of infusing fluid directly into a vessel wall. For example, a device for medicating a vessel wall is disclosed in U.S. Pat. Nos. 5,112,305 and 5,242,397 which issued to Barath et al. Specifically, the device disclosed in the Barath et al. patents employs a balloon which initially is slowly filled with a medicament to expand the balloon and position the balloon's surface against the vessel wall. Subsequently, the balloon is rapidly filled. The rapid filling of the balloon reconfigures tubular extensions on the surface of the balloon for insertion into the vessel wall and infusion of medicaments through the tubular extensions.

However, this device has proved not to be entirely satisfactory. Specifically, with this device, the mechanism for infusing a fluid into a vessel wall is not independent and separately operable from the mechanisms which position the device in the artery and which cause penetration into the vessel wall. Further, this device does have the capability of selectively applying a variable force to the fluid injectors of the device as they penetrate into the vessel wall.

In light of the above, it is an object of the present invention to provide a device for injecting fluid into a wall of a vessel having a mechanism for penetrating the vessel wall that is separate from the mechanism which injects the fluid into the vessel wall. It is another object of the present invention to provide a device for injecting fluid into the wall of a vessel which can selectively vary the force that is used to penetrate the vessel wall. Still another object of the present invention is to provide a device for injecting fluid into the wall of a vessel which is easy to use, and relatively simple and inexpensive to manufacture. Yet another object of the present invention is to provide a device for injecting radioactive isotopes into a wall of a vessel.

SUMMARY OF THE INVENTION

In accordance with the present invention, a device for injecting a fluid from a fluid source into a treatment area of a wall of a vessel includes an expander and one or more injectors. Preferably, the device includes a plurality of injectors for distributing the fluid into a larger treatment area.

In a first version of the present invention, the expander includes a balloon which is expandable from a contracted, first configuration to an expanded second configuration. The injectors extend radially from the balloon and move radially with the balloon between the first configuration and the second configuration. The injectors penetrate the treatment area and selectively release the fluid when the balloon is at the second configuration. Further, the balloon can simultaneously dilate the vessel when the balloon is in its second configuration.

As provided below, an inflator selectively controls the expansion of the balloon and the fluid source selectively provides a pressurized supply of fluid to the injectors. Thus, the mechanism which causes the injectors to penetrate the vessel wall is separate from the mechanism which releases the fluid into the vessel wall.

At least one fluid passageway connects the fluid source in fluid communication with the injectors. For example, the fluid passageway can include a flexible tubular sleeve which substantially encompasses and encloses at least a portion of an outer surface of the balloon. The tubular sleeve cooperates with the outer surface of the balloon to form a portion of the fluid passageway. In this embodiment of the fluid passageway, a distal end of the tubular sleeve attaches directly to the outer surface of the balloon and an open proximal end of the sleeve extends proximally from the balloon for connection with the fluid source.

Each injector can be a substantially tubular protrusion having an attachment end and an open cutting edge. The attachment end includes a base plate which mounts directly onto the tubular sleeve. In an alternate embodiment of the injectors, a plurality of tubular protrusions can be mounted onto the same base plate.

Each tubular protrusion includes a fluid channel through the injector which is placed in fluid communication with the fluid passageway. To establish a fluid path from the fluid source to the fluid channel, the base plate of the injector can be mounted onto the tubular sleeve over holes that may either be preformed into the tubular sleeve or formed into the tubular sleeve after the injectors have been attached to the tubular sleeve.

As intended for the present invention, the inflator can be directly connected to a lumen of a catheter. The catheter lumen, in turn, is in fluid communication with an interior of the balloon to inflate and deflate the balloon between the first and second configurations.

The fluid source includes a fluid pump which is in fluid communication with the fluid passageway for selectively providing a pressurized supply of fluid from the fluid source to the injectors.

The invention is also a method for expanding the treatment area and delivering fluid from the fluid source to the treatment area. The method includes advancing the balloon in the vessel while the balloon at its first configuration, expanding the balloon to its second configuration and selectively releasing the fluid from the injector into the treatment area. Basically, the balloon is advanced in the vessel until the balloon is positioned substantially adjacent the treatment area. Subsequently, the balloon is expanded to its second configuration. The expansion of the balloon causes the cutting edge of at least one injector which moves with the balloon to penetrate the treatment area. The expansion of the balloon can also cause simultaneous dilation of the vessel.

Depending upon the fluid and the desired treatment, the fluid can be released substantially simultaneously with the cutting edge penetrating the treatment area or there can be a time delay between the cutting edge penetrating the treatment area and the release of the fluid from the injectors.

In a second version of the present invention, the expander includes a multi-lumen catheter and a grommet. The catheter and the grommet are both disposed about the same longitudinal axis with the grommet separated distally from the distal end of the multi-lumen catheter. Importantly, the grommet is movable in translation along the longitudinal axis to allow separation between the grommet and the multi-lumen catheter to either increase or decrease.

The second version includes a plurality of hollow, flexible, tubes which are each formed with a lumen and which each have a distal end, a central region, and a proximal end. The distal end of each of the tubes is attached to the grommet. The proximal end of each of the tubes is attached to the catheter. The attachment between the tubes and the catheter, as well as the attachment between the tubes and the grommet, arranges the plurality of tubes radially around the catheter. In this arrangement, the attachment between the multi-lumen catheter and the plurality of tubes is such that the lumen of each tube is connected in fluid communication with a respective lumen of the multi-lumen catheter. As a result, fluid may be supplied under pressure to pass through the multi-lumen catheter and into the plurality of tubes. In general, each tube is connected to an individual lumen within the catheter. Alternatively, the plurality of tubes may be connected singly, or in combination, to one or more common lumens within the multi-lumen catheter.

In the second version of the expander, the plurality of injectors are attached to the central region of each flexible tube and project radially outward from the longitudinal axis. The fluid is passed through the multi-lumen catheter, the lumens of the flexible tubes and out of the injectors.

For the second version, a push-pull wire is connected to the grommet and passed through one of the lumens of the multi-lumen catheter. The insertion of the push-pull wire through the multi-lumen catheter allows the push-pull wire to be moved translationally along the longitudinal axis of the present invention. Furthermore, the translational movement of the push-pull wire causes the grommet to move translationally with respect to the multi-lumen catheter. In this fashion, the push-pull wire may be used to increase, or decrease, the separation between the grommet and the multi-lumen catheter.

As provided in detail below, as the separation between the grommet and the multi-lumen catheter decreases, each of the flexible tubes arches, or bows, outwardly, from the longitudinal axis, giving the device an expanded configuration. Alternatively, as the push-pull wire is advanced to increase the separation between the grommet and the multi-lumen catheter, each of the flexible tubes straightens, or flattens, giving the device a contracted configuration.

It is important to recognize that a device in accordance with the present invention utilizes a mechanism which causes the injectors to penetrate the vessel wall that is separate from the mechanism which releases the fluid into the vessel wall. Further, the device can vary the force that is used to penetrate the vessel wall and can simultaneously dilate the vessel wall. Additionally, the present invention is particularly useful for injecting radioactive isotopes directly into the vessel wall.

BRIEF DESCRIPTION OF THE DRAWINGS

The novel features of this invention, as well as the invention itself, both as to its structure and its operation will be best understood from the accompanying drawings, taken in conjunction with the accompanying description, in which.

DESCRIPTION

Figure 1:
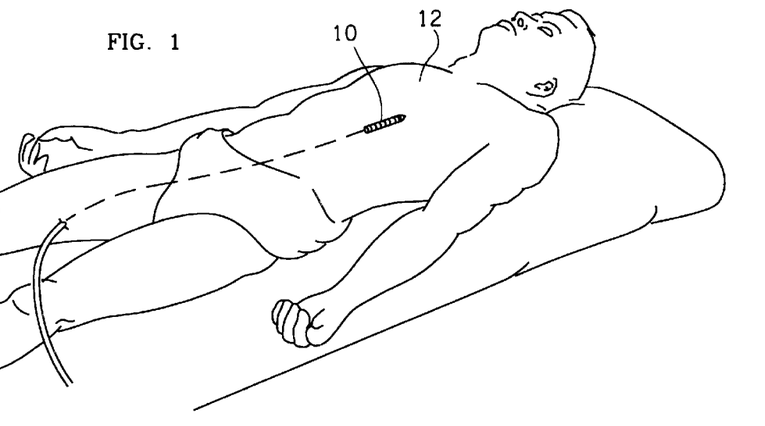
FIG. 1 is a perspective view of a patient with a device having features of the present invention positioned in an artery of the patient.

Referring initially to FIG. 1, a device 10 for injecting a fluid 13 into a wall of a blood vessel 11 in accordance with the present invention is shown positioned in an upper body, blood vessel 11 of a patient 12. However, the use of the device 10 is not confined to only upper body blood vessels 11 but, instead, can be used in arteries and vessels throughout the patient 12. Importantly, as provided in detail below, the device 10 provided herein, allows for symmetric injection of the fluid 13 directly in the vessel 11 around the circumference of the vessel 11.

Figure 2:
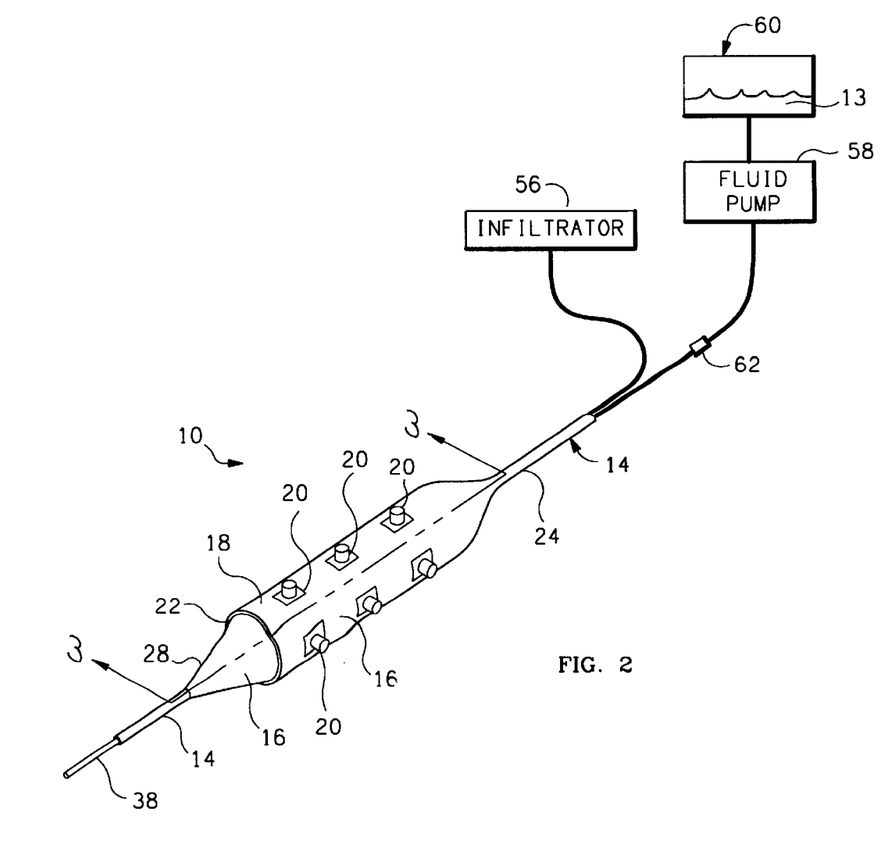
FIG. 2 is a perspective view of a device having features of the present invention.

Referring to FIG. 2, a first version of a device 10 having features of the present invention includes a multi-lumen catheter 14, an expander mounted thereon, a tubular sleeve 18 and a plurality injectors 20.

As shown in FIGS. 2–7, the expander can be an inflatable balloon 16. The balloon 16 is at least inflated and deflated between a first, substantially retracted configuration and a second, substantially expanded configuration. The balloon 16 when at the first configuration is substantially deflated. The balloon 16 when at the second configuration can be anywhere from the partially inflated to fully inflated depending upon the size of the vessel 11. For purposes of the present invention, the balloon 16 and tubular sleeve 18 are preferably made of polyethylene terephthalate (PET).

Further, FIG. 2 indicates that the tubular sleeve 18 surrounds a substantial portion of the balloon 16, and that a plurality of injectors 20 are mounted onto the tubular sleeve 18. Of these, the injectors 20 shown are only exemplary.

Figure 3:
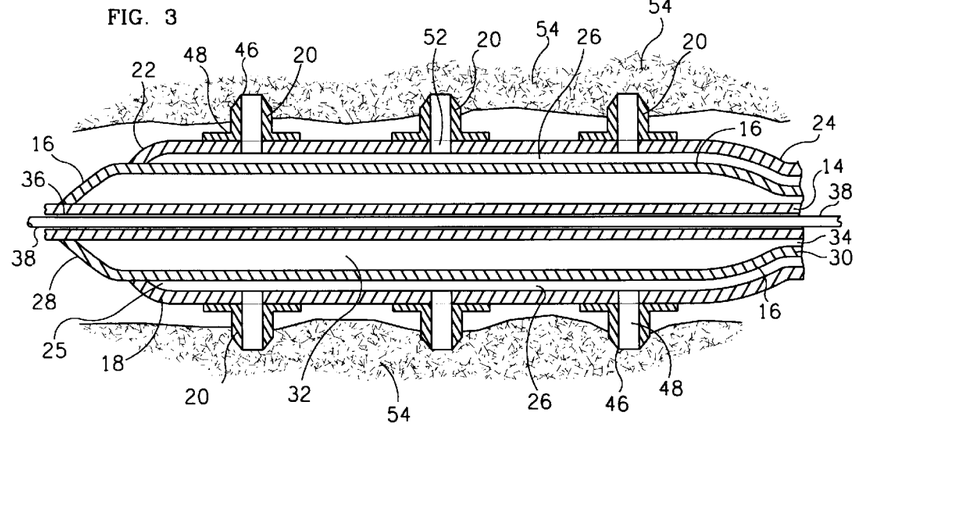
FIG. 3 is a cross-sectional view of the device of FIG. 2 taken on line 3—3 in FIG. 2 positioned in an artery of a patient.

A more complete appreciation of the structural cooperation between balloon 16, tubular sleeve 18 and the injectors 20 is provided by FIG. 3 wherein, it will be seen that a distal end 22 of tubular sleeve 18 is attached directly to an outer surface 25 of balloon 16. FIG. 3 also shows that the tubular sleeve 18 substantially surrounds and encloses the balloon 16 and that a proximal end 24 of tubular sleeve 18 extends proximally from and beyond the balloon 16 over catheter 14. The tubular sleeve 18 cooperates with the outer surface 25 of the balloon 16 to define a portion of a fluid passageway 26. The proximal end 24 can be connected to an outer lumen 27 (not shown in FIG. 3) of the catheter 14 to complete the fluid passageway 26.

FIG. 3 further shows that the distal end 28 of balloon 16 is affixed to the catheter 14, and that the proximal end 30 of the balloon 16 closes onto the catheter 14 to create an inflation chamber 32 in the interior of the balloon 16. A balloon port 34 provides fluid access into the inflation chamber 32. For purposes of the present invention, the balloon port 34 can be connected in fluid communication with a balloon lumen (not shown) of the catheter 14. FIG. 3 also shows that catheter 14 is formed with an inner lumen 36 which is dimensioned to receive a guidewire 38 therethrough.

Figures 4A, 4B, 5A, 5B:
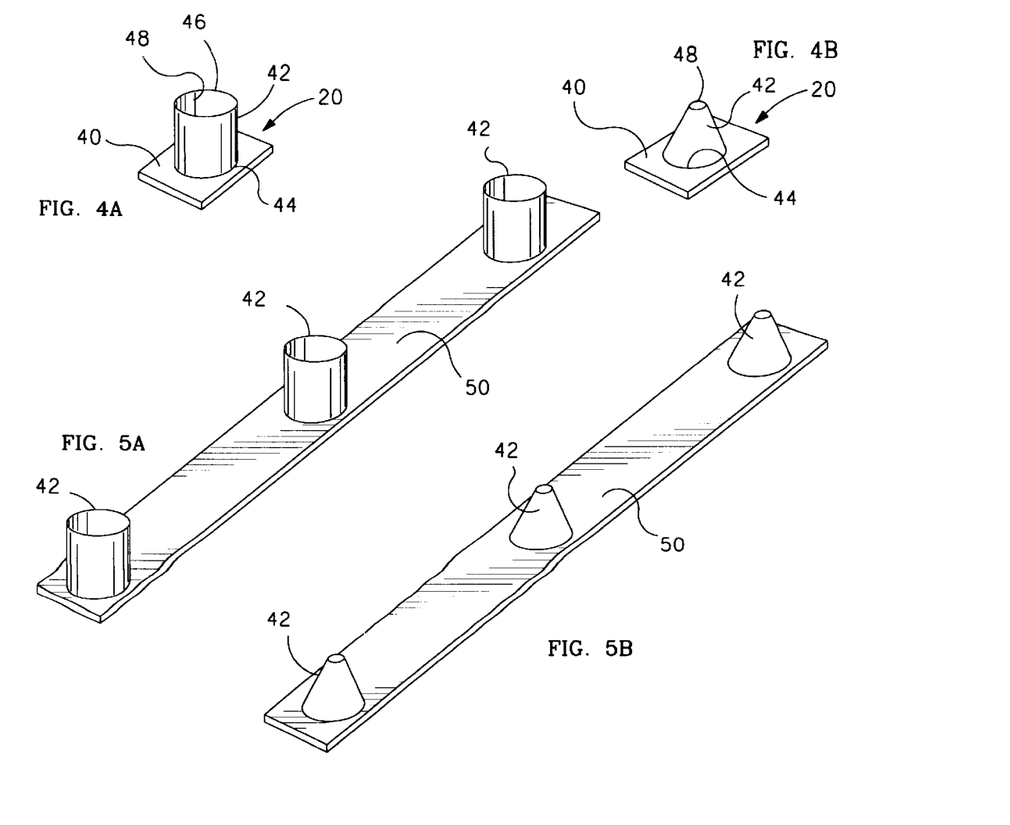
FIG. 4A is a perspective view of an embodiment for an injector having features of the present invention.
FIG. 4B is a perspective view of another embodiment for an injector having features of the present invention.
FIG. 5A is a perspective view of an embodiment of a plurality of injectors having features of the present invention.
FIG. 5B is a perspective view of another embodiment of a plurality injector of the present invention.

Referring now to FIG. 4A, each injector 20 includes a base plate 40 and a tubular protrusion 42 having an attachment end 44 and a cutting edge 46. Further, it is seen that the attachment end 44 of the tubular protrusion 42 affixes to and is an integral part of the base plate 40. Preferably, the injector 20 is made of nickel and the tubular protrusion 42 is formed by punching out the base plate 40. The cutting edge 46 is opposite the base plate 40. The tubular protrusion 42 defines a fluid channel 48 which extends through the injector 20. Each injector 20 shown in FIG. 4A is substantially annular shaped.

FIG. 4B shows another embodiment of the injector 20. Each tubular protrusion 42 shown in FIG. 4B is substantially conical shaped. Similarly, the injector 20 in FIG. 4B is preferably made of nickel and is formed to have a fluid channel 48 which extends through the injector 20.

FIG. 5A shows a plurality of injectors 20 formed upon the same base plate 50. Specifically, FIG. 5A shows an elongated base plate 50 from which the tubular protrusions 42 have been formed. In all important respects, the protrusions 42 shown in FIG. 5A are structurally the same as the tubular protrusion 42 discussed above with reference to FIG. 4A. The only difference being that they are collectively mounted on the same base plate 50.

Similarly, FIG. 5B shows a plurality injectors 20 formed upon the same base plate 50. In all important respects, the protrusions 42 shown in FIG. 5B are structurally the same as the tubular protrusion 42 discussed above with reference to FIG. 4B. Again, the only difference being that they are collectively mounted on the same base plate 50.

In the embodiment shown in FIG. 3, the injectors 20 are mounted onto the tubular sleeve 18 so that the fluid channel 48 of each respective injector 20 is aligned with a hole 52 in the tubular sleeve 18. This is done to establish fluid communication between the particular injector 20 and the fluid passageway 26. As a practical matter, it may be preferable in the construction of the device 10 to first mount the injector 20 onto the tubular sleeve 18, which can be done in any manner well known in the pertinent art, such as by bonding, and then pierce the tubular sleeve 18 through the fluid channel 48.

The injectors 20 of the present invention extend between about 0.005 inches and about 0.02 inches away from the tubular sleeve 18 when the balloon 16 is inflated.

Figure 6:
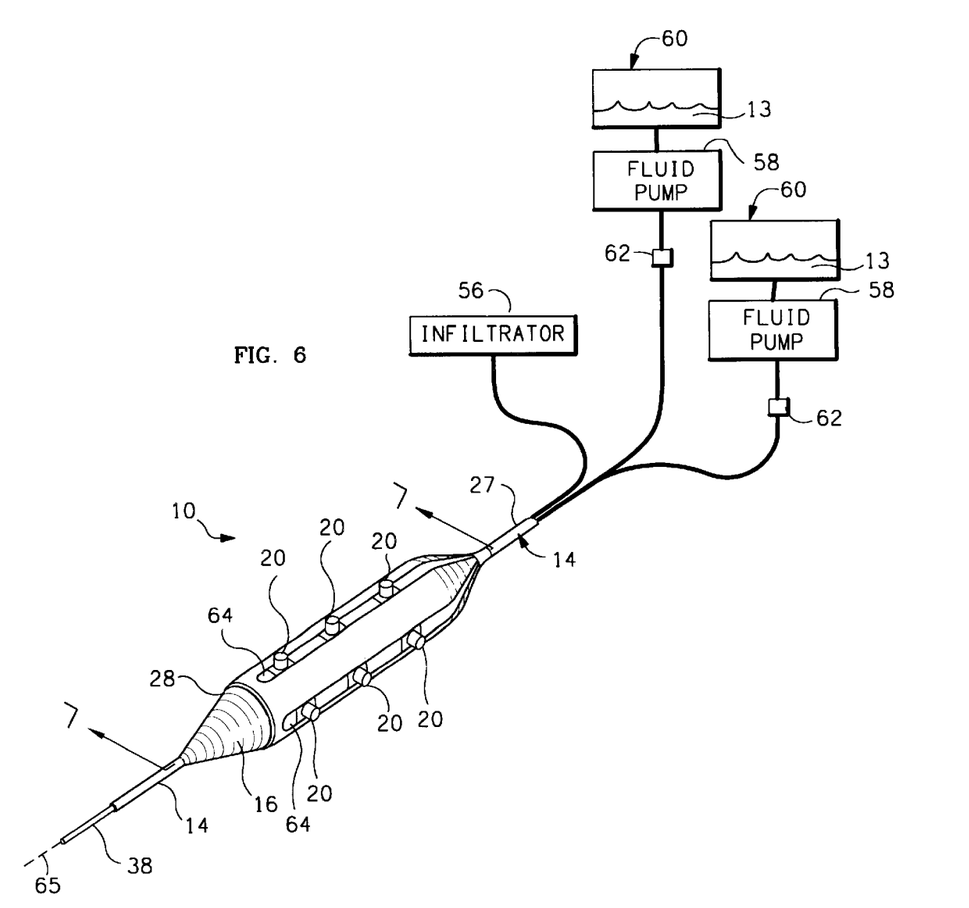
FIG. 6 is a perspective view of another embodiment of a device having features of the present invention.

In another embodiment of the present invention shown in FIG. 6, the basic components of the device 10 include the multi-lumen catheter 14 formed to accommodate the guide wire 38, the balloon 16, the plurality of injectors 20 and a plurality of tubular channels 64 mounted on the outer surface 25 of balloon 16. Each tubular channel 64 has a smaller diameter than the balloon 16 and is positioned to be substantially parallel with a longitudinal axis 65 of the balloon 16.

FIG. 6 further shows that mounted on the surface of each tubular channel 64 is the injectors 20. The injectors 20 are positioned on the surface of tubular channel 64 so that when balloon 16 is inflated, the injectors 20 move outwardly in a radial direction. Note, however, the showing of injectors 20 is for illustration purposes only and it should be appreciated that any injector 20 or combination of injectors 20 discussed in association with the previous embodiments may be used.

Figure 7:
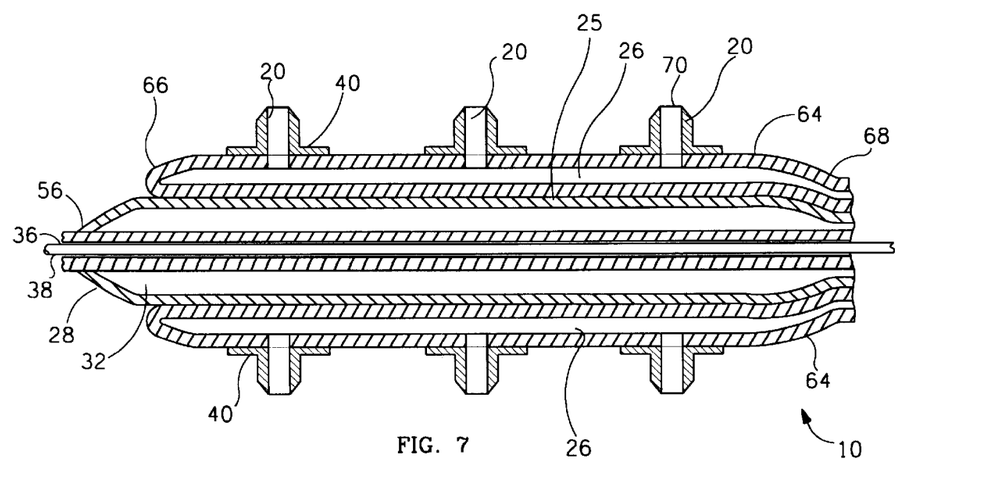
FIG. 7 is a cross-sectional view taken on line 7—7 of FIG. 6.

Referring now to FIG. 7, the cross-sectional view of device 10 shows the tubular channel 64 in more detail. More specifically, a distal end 66 of tubular channel 64 is sealed to create a portion of the fluid passageway 26 which connects the injectors 20 to the fluid source 60. Referring to FIGS. 6 and 7, it is appreciated that the proximal (extracorporeal) end 68 of the tubular channel 64 is in fluid communication with the outer lumen 27 of the catheter, which is connected in fluid communication with the fluid pump 58 and the fluid source 60.

Returning to FIG. 7, the injectors 20 are shown mounted on the surface of tubular channel 64. As FIG. 7 further shows in detail, base 40 of each injector 20 is mounted on the tubular channel 64 over a corresponding hole 70. From this view, it can be appreciated that any number of tubular channels 64 could be mounted on the external surface of balloon 16. It is further appreciated that any number of injectors 20 could be mounted on a single tubular channel 64.

The composition of the fluid 13 to be injected into the vessel 11 depends upon the treatment being performed and the physical characteristics of the patient 12. For example, depending upon the patient 12 and the treatment, the fluid 13 can be antibodies such as receptor site monoclonal antibodies, a toxic agent such as saponin, a genetic material such as DNA, a cellular material such as endothelial cells and/or medicaments such as heparin.

Alternately, the fluid 13 could be a radioactive isotope. It is believed that radioactive isotopes injected into the vessel 11 reduce and inhibit tissue and/or cell growth of the vessel wall. Since the radioactive isotopes are injected directly in the vessel 11 and are symmetrically injected around the circumference of the vessel 11, relatively low energy radioactive isotopes can be utilized. A radioisotope such as technetium 99 or thallium 205, which have a relatively short half life can be utilized with the present invention. These relatively low energy radioactive isotopes should cause less trauma to the patient 12. Additionally, the radioisotope can be encapsulated within a suitable carrier such as aminomannose modified liposome, which is rapidly absorbed into smooth muscle cells.

Figure 8:
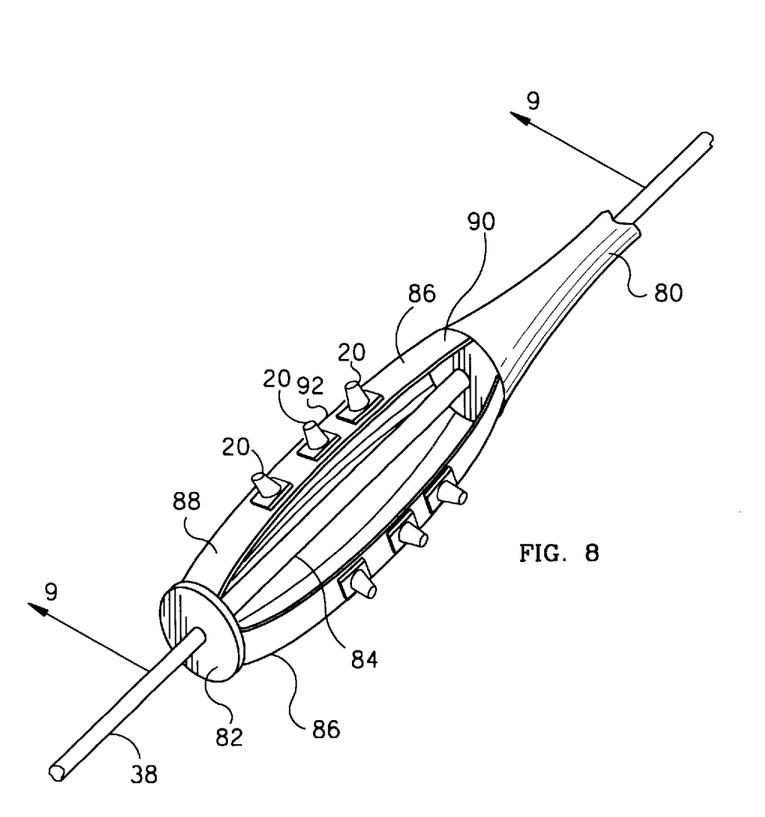
FIG. 8 is a perspective view of yet another embodiment of a device having features of the present invention.

FIG. 8 shows a second version of the expander which includes a multi-lumen catheter 80 and a grommet 82. Both the multi-lumen catheter 80 and the grommet 82 are disposed about the same longitudinal axis with the grommet 82 positioned distally, and separated from, the distal end of the multi-lumen catheter 80.

Some type of apparatus is used to move the grommet 82 translationally along the longitudinal axis. For example, referring to FIG. 8, a push-pull wire 84, is shown connected to the grommet 82. The push-pull wire 84 extends through one of the lumens of the multi-lumen catheter 80 allowing the push-pull wire 84 to move translationally in line with the longitudinal axis. The translational movement of the push-pull wire 84 causes the grommet 82 to undergo a similar translational displacement. In many cases, it will be desirable to use the device 10 of the present invention in combination with the guidewire 38. In such cases, the push-pull wire 84 may be formed with an internal lumen through which the guidewire 38 may be passed.

In the second version, a plurality of hollow, flexible tubes 86 are attached between the grommet 82 and the multi-lumen catheter 80. Each of the flexible tubes 86 includes a distal end 88, a proximal end 90 and a central region 92. The proximal end 90 of each tube 86 is joined to the multi-lumen catheter 80. The distal end 88 of each tube 86 is joined to the grommet 82. Preferably, the tubes 86 are distributed radially around the multi-lumen catheter 80 and grommet 82 in a manner substantially as shown in FIG. 8.

Figure 9:
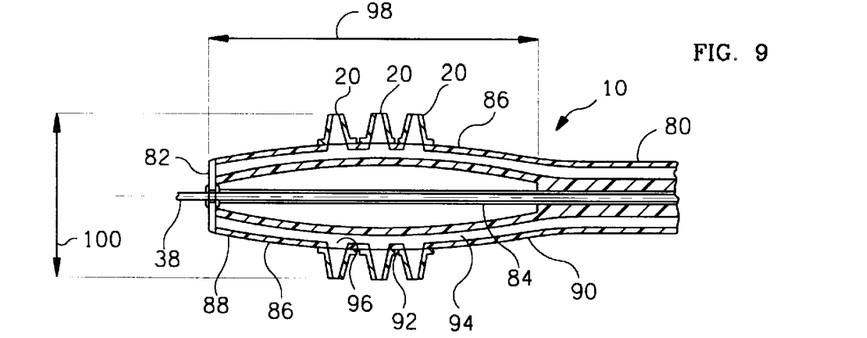
FIG. 9 is a cross-sectional view of the device of FIG. 8 shown in a retracted configuration, as seen along line 9—9 in FIG. 8.
Figure 10:
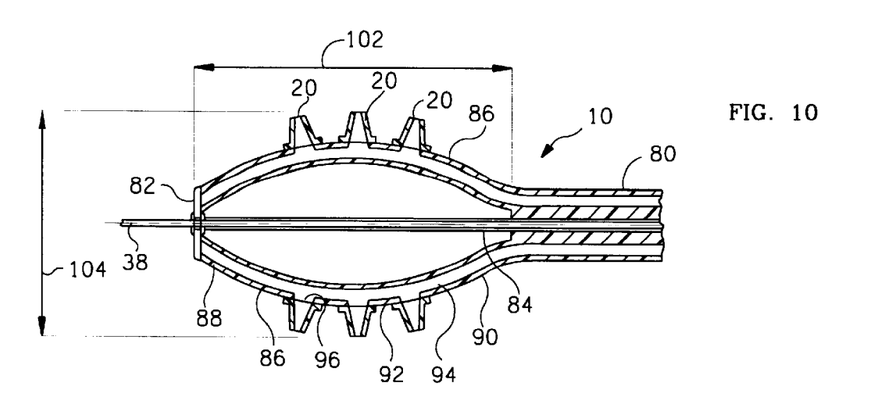
FIG. 10 is a cross-sectional view of the device of FIG. 8 shown in an expanded configuration, as seen along the line 9—9 in FIG. 8.
Figure 11:
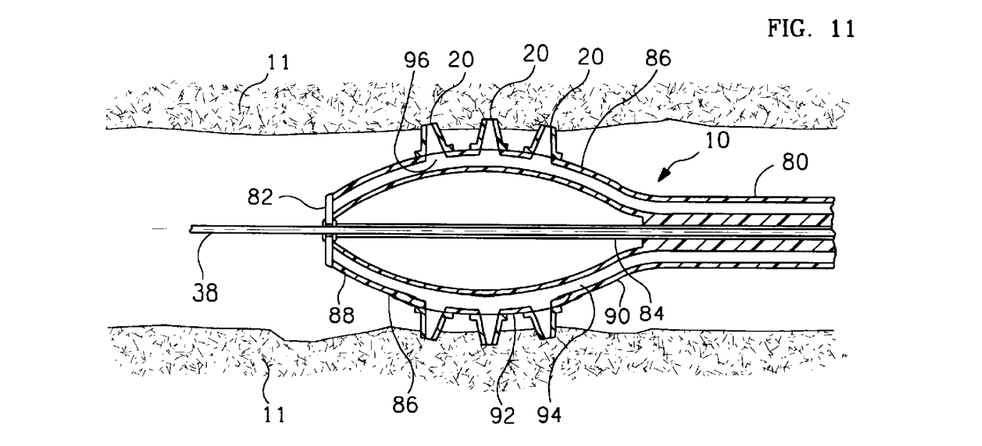
FIG. 11 is a cross-sectional view of the device of FIG. 8 positioned in a blood vessel of the patient.

Turning now to FIGS. 9 and 10, it may be seen that each flexible tube 86 is formed with a lumen 94. The lumen 94 of flexible tubes 86 passes through flexible catheter 80 allowing fluid 13 to be passed through multi-lumen catheter 80 and into flexible tubes 86. The lumen 94 of each flexible tube 86 passes separately through multi-lumen catheter 80 allowing a different fluid 13 to be passed into each flexible tube 86. Alternatively, the lumen 94 of each flexible tube 86 may be attached to one or more common lumens within multi-lumen catheter 80.

FIGS. 9 and 10 also show that the plurality of injectors 20 are attached to the central region 92 of each tube 86. Each flexible tube 86 is formed with a plurality of holes 96 which correspond to a respective injector 20. Functionally, each hole 96 connects the channel of a respective injector 20 to lumen 94 allowing the fluid pump 58 to pump fluid 13 from the fluid source 60 into lumen 94 to be expelled through the injectors 20.

FIGS. 9, and 10 also show that the present invention is movable between the first, contracted configuration (shown in FIG. 9) and the second, expanded configuration (shown in FIG. 10). In greater detail, it may be seen that the grommet 82 and the multi-lumen catheter 80 are distanced by a first separation 98. The device 10 shown in FIG. 9 also has a first overall width designated 100. In comparison, the grommet 82 and the multi-lumen catheter 80, shown in FIG. 10 is distanced by a second separation 102 which is smaller than the first separation 98 of FIG. 9. The device 10, shown in FIG. 10 also has a second overall width 104 which is greater than the first overall width 100 shown in FIG. 9.

The difference between the first, contracted configuration shown in FIG. 9 and the second, expanded configuration shown in FIG. 10 is accomplished, by translational movement of the grommet 82 along the longitudinal axis. In more detail, as the push-pull wire 84 causes the grommet 82 to move towards the multi-lumen catheter 80, each of the flexible tubes 86 bows outwardly away from the longitudinal axis. In this fashion, the push-pull wire 84 may be used to move the grommet 82 translationally to cause the flexible tubes 86 to alternately bow, as seen in FIG. 10, and straighten, as seen in FIG. 9. In some cases, it will be preferable to fabricate the flexible tubes 86 from resilient material which biases the tubes 86 into either the bowed or straight configuration.

OPERATION

An example of the operation of the balloon 16 version of the expander can best be visualized with initial reference to FIGS. 1–3. First, the guidewire 38 is positioned into the vessel 11 of the patient 12. This is done to establish a mechanical pathway through the vessel 11 to the treatment area 54 where the fluid 13 is to be released. The extracorporeal end of the guidewire 38 is then inserted into the catheter 14 lumen.

Next, the balloon 16, which is attached to the catheter 14, is moved over the guidewire 38 to the treatment area 54. The balloon 16 is at its first configuration during movement in the vessel 11. Once the balloon 16 is properly positioned proximate the treatment area 54, an inflator 56 is activated to inflate the balloon 16 to its second configuration. As shown in FIG. 2, the inflator 56 is connected to the proximal (extracorporeal) end of the device 10.

Referring back to FIG. 3, it will be appreciated that, as the balloon 16 is inflated, the expanding balloon 16 urges against the tubular sleeve 18 and causes the tubular sleeve 18 to likewise expand. Consequently, the injectors 20 mounted on the tubular sleeve 18 move radially from the catheter 14 and embed into the treatment area 54. Further, the balloon 16 can be used to simultaneously dilate the balloon.

With the injectors 20 embedded into the treatment area 54, the fluid pump 58 shown in FIG. 2 is activated to pump fluid 13 from the fluid source 60 into the fluid passageway 26. Importantly, this pumping action also causes any fluid 13 which has already been pumped into the fluid passageway 26 to be expelled through the fluid channels 48 of injectors 20 and into the tissue of treatment area 54.

Alternatively, the fluid pump 58 could be activated prior to embedding the injectors 20 into the vessel wall 11 and a valve 62 could be used to prevent the flow of fluid 13 until the injectors 20 are embedded in the treatment area 54. The valve 62 can then be opened when the injectors 20 penetrate into the treatment area 54 so that injection occurs substantially simultaneously with the embedding of the injectors 20 in the treatment area 54. Alternately, the injection of the fluid 13 could happen after a time delay by waiting to open the valve 62 for at least about one second to about twenty seconds.

After the fluid 13 from the fluid source 60 has been infused into the treatment area 54, the balloon 16 can be deflated to the first configuration by reversing the inflator 56. This action will cause the balloon 16 to collapse and withdraw the injectors 20 from the treatment area 54. The entire device 10 can then be withdrawn from the patient 12 over the guidewire 38.

The embodiment shown in FIGS. 6 and 7 utilizes a plurality of individual, tubular channels 64. With this embodiment, it is possible to either maintain fluid communication with, or fluid isolation between, each tubular channel 64. For example, fluid communication between each tubular channel 64 can be established by fluidly connecting each tubular channel 64 together within one outer lumen 27 of the catheter 14 so that each tubular channel 64 is supplied fluid 13 from the same fluid pump 58. Alternatively, fluid isolation may be maintained between each tubular channel 64 by providing each tubular channel 64 with a corresponding and independent outer lumen 27 and establishing its own fluid connection to a corresponding and independent fluid pump 58. Consequently, it is possible to inject a variety of alternate fluids 13 simultaneously by using a plurality of tubular channels 64 which are each connected to a separate fluid pump 58.

While the particular device 10 for injecting fluid 13 into the treatment area 54 as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A method for delivering a fluid from a fluid source to a treatment area in a wall of a vessel, the method comprising the steps of:

advancing a balloon in a vessel, while the balloon is at a first configuration, until the balloon is positioned substantially adjacent the treatment area, the balloon having a tubular sleeve which encircles at least a portion of the balloon;

expanding the balloon to a larger, second configuration so that a penetrating cutting edge of at least one injector, which is attached to an outer surface of the tubular sleeve and moves with the balloon, penetrates the wall of the vessel; and selectively releasing the fluid from the at least one injector into the wall of the vessel.

2. The method of claim 1 wherein the step of selectively releasing the fluid occurs substantially simultaneously with the cutting edge penetrating the treatment area.

3. The method of claim 1 comprising the step of waiting for at least about one second between the step of expanding the balloon and the step of selectively releasing the fluid.

4. The method of claim 1 wherein the step of selectively releasing the fluid includes releasing antibodies.

5. The method of claim 1 wherein the step of selectively releasing the fluid includes releasing a toxic agent.

6. The method of claim 1 wherein the step of selectively releasing the fluid includes releasing a genetic material.

7. The method of claim 1 wherein the step of selectively releasing the fluid includes releasing a cellular material.

8. The method of claim 1 wherein the step of selectively releasing the fluid includes releasing cells.

9. The method of claim 1 wherein the step of selectively releasing the fluid includes releasing a radioactive isotope.

10. The method of claim 1 wherein the step of selectively releasing the fluid includes releasing a liposome.

11. A method for treating a treatment area in a wall of a vessel, the method comprising the steps of:

advancing an expanding member in a vessel, while the expanding member is at a first configuration, until the expanding member is positioned substantially adjacent to the treatment area;

expanding the expanding member to a larger, second configuration so that a penetrating cutting edge of at least one injector, which is attached to an outer surface of the expanding member and moves with the expanding member, penetrates the wall of the vessel; and selectively releasing a radioactive isotope from the at least one injector into the treatment area.

12. The method of claim 11 wherein, the step of selectively releasing the radioactive isotope includes selectively releasing technetium 99.

13. The method of claim 11 when the step of releasing the radioactive isotope includes releasing thallium 205.

14. The method of claim 11 wherein, the expanding member is an inflatable balloon.

15. A device for treating a treatment area in a wall of a vessel, the device comprising:

an expanding member that at least can be moved between a first, contracted configuration and a second, expanded configuration;

a plurality of spaced apart injectors extending outwardly from the expanding member and moving with the expanding member between the first and second configurations, each injector comprises a substantially tubular protrusion defining a fluid channel, the tubular protrusion having an attachment end which is attached to the expanding member and an open, penetrating cutting edge which extends away from the expanding member for penetrating into the wall of a vessel;

a fluid source selectively providing a pressurized supply of radioactive isotopes; and at least one fluid passageway connecting the fluid source in fluid communication with the fluid channel for each injector.

16. The device of claim 15 wherein the expanding member is an expandable balloon.

17. The device of claim 15, wherein the expanding member comprises:

a catheter having a longitudinal axis;

a grommet;

a plurality of resilient tubes, each said tube formed with a tube lumen and having a proximal end, a distal end, and a central region, said proximal end of each said tube being attached to said catheter and said distal end of each said tube being attached to said grommet; and means for moving said grommet between a first position wherein said central region of each said tube is held substantially juxtaposed to said longitudinal axis and a second position wherein said central region of each said tube is radially distanced from said longitudinal axis.

18. A device as recited in claim 17 wherein said means for moving said grommet comprises a push-pull wire, said push-pull wire being attached to said grommet and extending through a catheter lumen in the catheter.

19. A device useful for injecting a fluid from a fluid source into a wall of a vessel, the device comprising:

an expanding member that at least can be moved between a contracted, first configuration and an expanded, second configuration;

an injector moving with the expanding member between the first and second configurations, the injector comprising a substantially tubular protrusion defining a fluid channel, the tubular protrusion having an attachment end and an open, penetrating cutting edge which extends away from the expanding member for penetrating into the wall of a vessel when the expanding member is in the second configuration; and at least one fluid passageway connecting the fluid source in fluid communication with the fluid channel of the injector.

20. The device of claim 19 including a tubular sleeve which substantially encircles a portion of the expanding member to create an infusion chamber.

21. The device of claim 20 wherein the tubular sleeve encircles substantially the entire expanding member.

22. The device of claim 20 wherein the injector is secured to an external outer surface of the tubular sleeve.

23. The device of claim 20 wherein the attachment end of the injector is attached to an external outer surface of the tubular sleeve.

24. The device of claim 19 wherein the expanding member is adapted to dilate the vessel at the second, expanded configuration.

25. The device of claim 19 including a plurality of injectors which are attached to a plurality of fluid passageways.

26. The device of claim 25 wherein the plurality of fluid passageways are mounted on an outer surface of the expanding member.

27. The device of claim 19 wherein the expanding member is an expandable balloon.

28. The device of claim 19, wherein the expanding member comprises:

a catheter having a longitudinal axis;

a grommet;

a plurality of resilient tubes, each tube being formed with a tube lumen which defines the at least one fluid passageway, each tube having a proximal end, a distal end, and a central region, the proximal end of each tube being attached to the catheter and the distal end of each tube being attached to the grommet; and means for moving the grommet between a first position wherein the central region of at least one of the tubes is held substantially juxtaposed to the longitudinal axis and a second position wherein the central region of at least one of the tubes is radially distanced from the longitudinal axis.

29. The device of claim 19, wherein the cutting edge extends away from the expanding member when the expanding member is in the first configuration.

* * * * *